United States Patent [19]

Boyce et al.

[11] Patent Number: 5,750,010
[45] Date of Patent: May 12, 1998

[54] PROCESS FOR PHOTOCHLORINATION

[75] Inventors: C. Bradford Boyce; Guy P. Pittman, both of Baton Rouge; Bolivar F. Lewis, III, Prairieville, all of La.

[73] Assignee: LaRoche Industries, Inc., Atlanta, Ga.

[21] Appl. No.: 537,355

[22] Filed: Oct. 3, 1995

[51] Int. Cl.$^6$ ..................................................... C07C 17/00
[52] U.S. Cl. .................. 204/157.94; 204/157.95; 204/158.11; 204/158.2
[58] Field of Search .................. 204/157.94, 157.95, 204/158.11, 158.2

[56] References Cited

U.S. PATENT DOCUMENTS

| | | | |
|---|---|---|---|
| 4,948,479 | 8/1990 | Brooks et al. | 204/157.94 |
| 5,190,626 | 3/1993 | Yates et al. | 204/157.95 |
| 5,326,918 | 7/1994 | Correia et al. | 204/158.11 |

OTHER PUBLICATIONS

Braun et al "Photochemical Technology". John Wiley & Sons, NY pp. 113 & 233 (1991) Month unavailable.

*Primary Examiner*—Kathryn Gorgos
*Assistant Examiner*—Edna Wong
*Attorney, Agent, or Firm*—Richard J. Hammond

[57] ABSTRACT

An improvement in the process for the photochlorination of liquid mixtures of 1,1-dichloro-1-fluoroethane and unsaturated hydrocarbons with ultraviolet light is disclosed. The improvement comprises using ultraviolet light emitted from an ultraviolet light source having an ultraviolet radiation efficiency of at least 0.01 Einsteins per inch of arc per 100 watts input at a wavelength that is substantially the same as the wavelength absorption band of chlorine.

6 Claims, No Drawings

PROCESS FOR PHOTOCHLORINATION

FIELD OF INVENTION

This invention relates to an improved process for the removal of unsaturated compounds from 1,1-dichloro-1-fluoroethane using photochlorination. In particular, this invention relates to an improvement in removing unsaturated compounds from liquid mixtures containing 1,1-dichloro-1-fluoroethane by photochlorination using an ultraviolet light source having an efficiency of at least 0.01 Einsteins\inch of arc\100 watts input power and emitting in a wavelength region that is substantially the same as the wavelength absorption band of chlorine.

BACKGROUND OF THE INVENTION

The saturated fluorocarbons and chlorofluorocarbons having from two to six carbon atoms are known to have superior chemical and thermal stability. Since they are relatively non-toxic and inert they have commercial utility as dielectric, hydraulic, etc. fluids. Additionally, the lower molecular weight compounds are used as propellants, refrigerants and the like. For example, trichlorofluoromethane is a heavily used blowing agent for urethane foams. The higher molecular weight compound 1,1,2-trichloro-1,2,2,-trifluoroethane is a used as a solvent for cleaning circuit boards. Unfortunately, these compounds and many of the other highly chlorinated lower aliphatic hydrocarbons are known to deplete the ozone layer once they are released into the atmosphere. The fluorinated compound, 1,1-dichloro-1-fluoroethane is considered to be a viable replacement for these and similar compounds.

Among the routes to the production of 1,1-dichloro-1-fluoroethane (referred to in the art as HCFC 141b), the reaction of vinylidene chloride or 1,1,1-trichloroethane with anhydrous hydrogen fluoride have enjoyed commercial success. While yields of the desired product are economically acceptable, contamination of this material with undesirable by-products can not be avoided. For example, typically residual starting material is present in the vinylidene chloride as well as a variety of reaction by-products which include other olefins. Because of the presence of these materials, it is difficult to separate HCFC 141b from the undesirable components in the reaction mix by conventional purification processes, i.e., distillation. In the trichloroethane reaction, vinylidene chloride is a by-product. In any case, several unsaturated by-products result from these reactions which must be separated from 1,1-dichloro-1-fluoroethane before it can be used in the manner intended.

In Organic Fluorine Chemistry by Sheppard et al, W. A. Benjamin Inc. N.Y., N.Y., 1969, p 452 inhalation toxicity data are given for polyfluorochlorocarbons from tests on rats or mice. The data show that the saturated fluorochlorocarbons are inert materials. Unsaturated analogs are, however, toxic.

Numerous methods have been published on methods to reduce the amount of unsaturated compounds in saturated hydrofluorochlorocarbons.

U.S. Pat. No. 2,999,885 discloses contacting a contaminated two to six carbon saturated fluorocarbon with an aqueous solution of potassium permanganate containing an alkali metal hydroxide will result in a purified saturated fluorocarbon.

U.S. Pat. No. 5,105,035 discloses a process for removing vinylidene chloride and other unsaturated impurities from HCFC-141b by reaction with hydrogen over a catalyst such as palladium on alumina.

European Patent 39311839 (1989) discloses purification of saturated fluorohalocarbons containing unsaturated impurities by the use of metal oxides to oxidize unsaturated impurities to carbon dioxide.

U.S. Pat. No. 3,004,075 discloses the preparation of a purified saturated two to six carbon fluorochlorocarbon by contacting the impure material with a mixture of pyridine and pyrrolidine or piperidine.

U.S. Pat. No. 3,696,156 teaches that a two to six carbon saturated fluoroperhalocarbon containing olefinic impurities can be purified by contacting the olefinic-contaminated fluoroperhalocarbon in the vapor phase with alumina impregnated with a basic alkali metal or alkaline earth metal hydroxide or oxide at 180° to 250° C.

U.S. Pat. No. 4,849,558 discloses that chlorofluorocarbon solvents contaminated with sulfur dioxide can be purified by contact with alumina or zeolite.

U.S. Pat. No. 4,950,816 discloses that 1,1-dichloro-1-fluoroethane containing olefinic impurities can be purified by passing the impure 1,1-dichloro-1-fluoroethane through activated carbon.

British Patent 627,773 (1949) discloses the purification of 1,1-dichloro-1-fluoroethane by chlorinating the contaminating vinylidene chloride and distilling the desired product overhead. The chlorination procedure is not described. However, vinylidene chloride is known to be stable to chlorine in the dark, e.g., see J.Chem. Soc. Faraday Trans.70 1419 (1974)), and 1,1-dichloro-1-fluoro-ethane is well known to be unstable to the Lewis acid catalysts such as $FeCl_3$ sometimes used to catayze chlorine additions. Accordingly, it is reasonable to assume that the chlorination was accomplised by exposing the mixture to light. Incandescent or fluorescent lamps and sunlight have sufficient output below 500 nm to initiate free radical chain reactions of chlorine.

SUMMARY OF THE INVENTION

An improved process for removing unsaturated carbon compounds from 1,1-dichloro-1-fluoroethane is disclosed. The improvement is applied to a process that first treats a liquid mixture of 1,1-dichloro-1-fluoroethane and at least one unsaturated carbon-containing compound with chlorine and by irradiation with ultraviolet light. This irradiation selectively converts at least a portion of the at least one unsaturated carbon-containing compound in the mixture to the corresponding photochlorinated product. The improvement in this process resides in the discovery of employing ultraviolet light using an efficient low power, phosphor coated low pressure mercury light source whose energy emmission band closely matches the chlorine absorption band with little loss of energy to unusable visible light or infrared (heat). Unlike medium and high pressure high power lamps. These lamps do not require special attention to heat removal from the system. Furthermore there is a significant reductution in the frequency with which the lamp wells must be cleaned. The irradiated composition from this improved process contains few or no tars typically found as contaminants in prior art high power photochlorination processes. Separation of the desired 1,1-dichloro-1-fluoroethane in high yields is therefore facilitated.

DETAILED DESCRIPTION OF THE INVENTION

The present invention comprises an improvement in a process for purifying saturated 2 to 6 carbon-containing aliphatic hydrofluorohalocarbons, particularly 1,1-dichloro-1-fluoroethane, containing olefinic impurities such as are illustrated by the hydrofluoroolefins and the hydrofluorochloroolefins.

In the process for manufacturing saturated 2 to 6 carbon containing aliphatic hydrofluorochlorocarbons and hydrofluorocarbons many undesirable by-products briefly described above are formed. These by-products arise from condensation, thermolysis, dehalogenation or the incomplete conversion of the reaction-product mixture. The by-products sometimes are not readily removed by conventional separation techniques such as fractional distillation, phase separation and the like. However, these olefinic materials are susceptible to photochlorination.

The term "photochlorination" as used herein is intended to mean the process by which a light induced reaction of chlorine with unsaturated by-products of the 2 to 6 carbon-containing aliphatic hydrofluorohalocarbon process occurs. The photochlorination process converts the olefins to higher molecular weight materials that exhibit chemical and physical properties substantially different than the properties of the desired 2 to 6 carbon-containing aliphatic hydrofluorohalocarbon products. Separation of these photochlorinated materials from the desired products is considerably simplified.

In the photochlorination process, the crude mixture of 2 to 6 carbon-containing aliphatic hydrofluorohalocarbon (most preferably, the crude reaction mixture of 1,1-dichloro-1-fluoroethane) is advantageously separated from lower boiling contaminents by distillation to prevent the higher boiling chlorinated by-products from contaminating the desired product. For example, where crude mixtures of 1,1-dichloro-1-fluoroethane are utilized in the process of the present invention, typical low boiling halohydrocarbons are 1-chloro-1,1-difluoroethane and 1,1,1-trifluoroethane which boil at lower temperatures than 1,1-dichloro-1-fluoroethane or vinylidene fluoride and 1,1-dichlorofluoroethylene. Similarly, higher boiling halohydrocarbon contaminants may also be separated in a subsequent distillation step.

The resulting partially refined hydrofluorohalocarbon is then subjected to photochlorination.

To carry out the photochlorination, the partially refined material is first treated with chlorine (in vapor or liquid form). The amount of chlorine used will vary depending on its solubility in the partially refined hydrofluorohalocarbon and on the temperature and pressure of the system. For example, when using partially refined mixtures of 1,1-dichloro-1-fluoroethane containing the undesirable unsaturated hydrocarbon, from about one mole to about three moles, preferably one to one and one half moles, of elemental chlorine is used per mole of unsaturated hydrocarbon contained in the partially refined mixture.

It should be noted that the photolytically-induced chlorination reaction not only occurs with the unsaturated material but also to some extent with other hydrocarbons present in the mixture. Thus, these reactions are competing. Accordingly, while the reaction rate associated with photolytic chlorination of the unsaturated hydrocarbon is high, a slower photolytic chlorination reaction also occurs with the hydrofluorohalocarbon, causing a somewhat decreased yield of the final product. For example, when excess chlorine is used (more then the amount of chlorine required to photolytically react with the unsaturated hydrocarbon) in partially refined mixtures of 1,1-dichloro-1-fluoroethane, 1,1,2-trichloro-1-fluoroethane is formed. While equimolar amounts of unsaturated hydrocarbon and chlorine diminish this side reaction, the reaction with the unsaturated hydrocarbon is not as complete. Thus, small adjustments in chlorine are necessary to balance the completeness of reaction with the unsaturated hydrocarbon while minimizing the reaction with the hydrofluorohalocarbon.

After passing chlorine into the partially refined hydrofluorohalocarbon, the mixture is irradiated with ultraviolet light to complete the photolytic chlorination of the unsaturated hydrocarbons.

As an alternate photolysis process, it should be noted that sequential chlorination followed by irradiation may be changed to simultaneous chlorination and irradiation.

Contrary to the teachings of the prior art, the photolysis reaction of the unsaturated hydrocarbons in partially refined hydrofluorohalocarbon mixtures does not require high power lamps to achieve complete conversions with reasonable reaction times. The prior art "high power" lamps are typically, medium and high pressure mercury lamps which convert electrical energy to UV radiaton with less than 40% efficiency. Most of the energy is simply converted to heat. These lamps emit UV energy over a broad band especially in the short wavelengh region which cause side reactions in the reaction mass. Because of the heat evolved and the intense broad band UV emmision, the chambers in the vessels containing these lamps (referred to as "wells") often need frequent cleaning. Close attention must be paid to removing the heat generated around the lamps to prevent them from overheating and subsequent early burn-out, e.g., these bulbs typically reach temperatures in excess of 600° C. Lowering the bulb temperature is not an option since such low temperatures tend to extinguish the bulbs. Moreover the lifetime of these lamps are usually in the 1000 to 2000 hour range. Mercury low pressure and low power phosphor coated fluorescent bulbs emitting in the UVB range have a lifetime around 8000 to 10,000 hr. These bulbs are highly efficient typically converting between 75% and 85% of the electrical imput to a UV emmission spectrum almost identical to the chlorine UV absoption spectrum, which efficiently activates the chlorine radical and promotes the photochlorination reaction with few side effects. For example, since little heat is evolved and the lamps have a lower intensity with relatively narrow wavelenth emmission band, less deposition of decomposition products on the wells results. Because of the long lifetime of the bulbs, there is a considerable reduction of system maintenance.

The rate of the photolytic reaction of chlorine with vinylidene chloride as well as most halogenated unsaturates is directly proportional to the square root of the intensity of the irradiation. The intensity of a lamp's output is proportional to power multiplied by the wavelengths present which are absorbed by the reactant. That value is reported as quanta per mole or Einsteins. A typical prior art medium to high pressure mercury 10 kilowatt lamp yields about 0.5 Einsteins\inch of arc in the 250–500 nm range, which is the range of activation of the chlorine molecule (input power is about 167 watts per inch of arc). As noted above, at least 60% of the input power is converted to heat. The low power phosphor coated fluorescent lamps used in the process of the present invention are much more efficient yielding about 0.01 Einsteins per inch of arc with an input power of 1.5 watts per inch of arc in the wavelength region of interest with only 10–20% of the input power evolved as heat. Preferably, in carrying out the improvement of the present invention, one or more lamps emitting about 0.6 Einsteins\100 watts is used at a wavelength of from about 300 to 400 mμ, most preferbly 0.7 Einsteins\100 watts (72 inch bulb) with an input power of 1.5 watts per inch of arc at this wavelength.

It appears from the above that 50 low pressure mercury lamps (of 5 kiloatts input) are required to match the performance of 1 10 kilowatt high pressure lamp (assuming both have about the same arc length). However, the rate of photocatalyzed chlorination of olefins is proportional to the square root of the light intensity. Accordingly, 7 low pressure 100 watt phosphor-coated (700 watts total) match the performance of one 10 kilowatt high pressure lamp of similar arc length.

Upon completion of the photolytic chlorination as described above, the partially refined hydrofluorohalocarbon mixture containing the photolytically chlorinated (previously unsaturated) hydrocarbons is futher processed to separate the hydrofluorohalocarbon from the remainder of the mixture. Typically this separation is carried out by distillation since the photolytically chlorinated products are readily separated from the hydrofluorohalocarbon because of their difference in boiling point. For example, in the case of photolytically chlorinated mixtures of 1,1-dichloro-1-fluoroethane containing vinylidene chloride as the unsaturated hydrocarbon, the photolysis forms 1,1,1,2-tetrachloroethane (bp 130° C.) which is easily separated from 1,1-dichloro-1-fluoroethane (bp 37° C.).

The present invention is illustrated by the following examples which are added to this specification for illustration purposes only and are not to be regarded as limiting the invention in any manner.

EXAMPLE 1

The olefinic impurities of crude 1,1-dichloro-1-fluoroethane (HCFC-141b) were photochlorinated under varying conditions to determine the effectiveness of a UV light system for removal of these olefins from crude HCFC-141b. The system consists of exposure of the crude HCFC-141b to light emitted in the UV-B spectrum range. The UV light source was a commercially available high efficiency bulb encased in a quartz well. The type of bulb selected for the photochlorination system has a phosphor coating that concentrates the emitted light in the 275 to 375 nm range.

Crude HCFC-141b contaminated with vinylidene dichloride (VDC) was mixed with chlorine ($Cl_2$) and exposed to the UV light. The reaction temperature varied from 38°–66° C. The reaction was done in the liquid phase and the pressure was controlled to keep the reactants in the liquid phase. The reactor pressure typically ranged from 15–60 psig. The samples were analyzed for VDC and chlorine both before and after the exposure to the UV light. The results are found in Table 1.

TABLE 1

| Sample No. | Residence time (hours) | VDC conc. inlet (ppm) | $Cl_2$ conc. inlet (ppm) | VDC conc. outlet (ppm) | $Cl_2$ conc. outlet (ppm) | Percent VDC reacted (%) |
| --- | --- | --- | --- | --- | --- | --- |
| 1 | 2.8 | 15,223 | 7,021 | 9,213 | 136 | 39.5 |
| 2 | 2.5 | 3,996 | 2,213 | 93 | 177 | 97.7 |
| 3 | 2.6 | 3,615 | 7,298 | 290 | 2,149 | 92.0 |
| 4 | 2.6 | 4,043 | 18,600 | 24 | 407 | 99.4 |
| 5 | 2.6 | 4,834 | 6,465 | 8 | 27 | 99.8 |

As observed in samples 2 through 5, the efficiency of VDC reaction is quite high. The amount of chlorine was not sufficient for the quantity of VDC in the sample 1. The average conversion of VDC for samples 2 through 5 was 97.2%. This system performs better than standard commercial photochlorination systems that employ low efficiency UV lights.

EXAMPLE 2

This Example is similar to Example 1 as to the quality of the crude HCFC-141b, the photochlorination apparatus, and the reaction conditions. The reaction residence time varied from 4.2 to 2.0 hours. A detailed examination of the sample outlet composition was done with a Varian 3400 gas chromatograph with flame ionization detector. The GC column used was model SPB-1701 with a 60 m length, 0.25 mm I.D., and 1.0 mm film thickness. The chlorine concentration was determined with common wet laboratory techniques. The effect of the photochlorination on the HCFC-141b present was also determined with this Example. The components of interest in this Example are listed in Table 2. The results of the experimentation for this Example are listed in Table 3.

TABLE 2

| Symbol | Compound |
| --- | --- |
| A | HCFC-141b |
| B | VDC |
| C | Chlorine |

TABLE 3

| Sample No. | A conc in ppm | B conc in ppm | C conc in ppm | A conc out % | B conc out ppm | C conc out ppm | % A reacted | % B reacted |
| --- | --- | --- | --- | --- | --- | --- | --- | --- |
| 1 | 98.80 | 5,302 | 9,985 | 98.19 | 0 | 38 | 0.61 | 100.00 |
| 2 | 99.00 | 4,558 | 12,753 | 98.15 | 0 | 7 | 0.86 | 100.00 |
| 3 | 99.21 | 3,331 | 4,555 | 98.86 | 94 | 1,577 | 0.35 | 97.12 |
| 4 | 99.16 | 3,993 | 4,341 | 98.80 | 0 | 114 | 0.36 | 100.00 |
| 5 | 99.05 | 4,891 | 5,059 | 98.95 | 548 | 80 | 0.10 | 88.80 |
| 6 | 99.05 | 5,309 | 5,416 | 98.83 | 31 | 49 | 0.22 | 99.42 |
| 7 | 98.90 | 6,491 | 4,041 | 98.83 | 405 | 56 | 0.07 | 93.76 |
| 8 | 98.78 | 5,765 | 7,697 | 98.66 | 75 | 778 | 0.13 | 98.70 |
| 9 | 98.78 | 5,821 | 7,190 | 98.29 | 7 | 195 | 0.49 | 99.88 |
| 10 | 98.84 | 5,721 | 23,778 | 97.63 | 0 | 212 | 1.23 | 0.00 |
| 11 | 98.98 | 4,730 | 11,083 | 98.07 | 0 | 1,101 | 0.91 | 100.00 |
| 12 | 98.72 | 8,211 | 9,580 | 98.06 | 0 | 47 | 0.67 | 100.00 |

The above results show an average VDC conversion of 98.14% and an average HCFC-141b conversion of 0.5%. These results are better than standard commercially available low efficiency UV light photochlorination systems in the extent of VDC reaction and the extent of undesirable HCFC-141b reaction. The photochlorination product of the reaction of chlorine and VDC was determined to be the expected 1,1,1,2-tetrachloroethane. The photochlorination product of HCFC-141b and chlorine was determined to be the expected 1,1,2-trichloro-1-fluoroethane. The data shows that the amount of excess chlorine over the required amount for reaction with VDC does determine the extent of undesirable HCFC-141b chlorination. Both the photochlorination products of VDC and HCFC-141b reaction with chlorine are separable from the HCFC-141b by common distillation techniques. The boiling points of the components of interest are listed in Table 4.

TABLE 4

| Component | Boiling Point (C.) |
| --- | --- |
| HCFC-141b | 32 |
| VDC | 37 |
| 1,1,2-trichloro-1-fluoroethane | 88 |
| 1,1,1,2-tetrachloroethane | 130.5 |

EXAMPLE 3

Information obtained from the above runs (see Examples 1 and 2) showed that commercially available, high efficiency lights emitting in the UV-B spectrum range gave results superior to those reported in U.S. Pat. No. 4,948,479. Using the same apparatus and procedures as described in the above Examples, variables where studied to determine their impact on the system. These variables were residence time, input power usage, mixing, and molar ratio of chlorine to VDC. The various run conditions are given in Table 5 below.

TABLE 5

| Run No. | Residence Time hours | Input Power Watt*hrs/kg | Mixing | Cl2 to VDC Ratio |
| --- | --- | --- | --- | --- |
| 1 | 2.1 | 0.217 | Yes | 1.5 |
| 2 | 2.1 | 0.289 | No | 2.5 |
| 3 | 2.1 | 0.289 | Yes | 1.5 |
| 4 | 2.1 | 0.217 | No | 2.5 |
| 5 | 2.6 | 0.361 | Yes | 2.5 |
| 6 | 2.6 | 0.271 | No | 1.5 |
| 7 | 2.6 | 0.361 | No | 1.5 |
| 8 | 2.6 | 0.271 | Yes | 2.5 |

HCFC-41b contaminated with, on average, 4330 ppm VDC was used as a feed for this Example. Light sources with U.V. intensity of about 0.7 Einsteins/100 Watts were used in this Example. The results are given in Table 6, below.

TABLE 6

| Run No. | VDC outlet conc. (ppm) | Chlorine outlet conc. (ppm) | HCFC-141b outlet conc. (%) | VDC reacted (%) | HCFC-141b reacted (%) |
| --- | --- | --- | --- | --- | --- |
| 1 | 387 | 210 | 98.5442 | 91.50 | 0.32 |
| 2 | 3 | 40 | 98.2784 | 99.91 | 0.58 |
| 3 | 393 | 148 | 98.6803 | 90.79 | 0.26 |
| 4 | 0 | 150 | 98.1816 | 100.00 | 0.61 |
| 5 | 47 | 151 | 97.9437 | 98.88 | 1.07 |
| 6 | 16 | 42 | 98.6723 | 99.60 | 0.33 |
| 7 | 59 | 48 | 98.7425 | 98.60 | 0.26 |
| 8 | 80 | 190 | 98.0573 | 98.02 | 1.2 |

The above results show that high efficiency UV light sources are effective to react out VDC from HCFC-141b with minimal degradation of the HCFC-141b product. Optimized run conditions, for example, runs 2, 4 and 6, show near complete reaction of the VDC can be obtained with minimal, for example, 0.33%, HCFC-141b degradation. The above results show that at the higher chlorine to VDC ratios the average HCFC-141b degradation is higher, 0.865%, than at the lower chlorine to VDC ratios, 0.292%.

Results generated from this Example show that the complete reaction of VDC from HCFC-141b can be achieved with significantly lower power(ie. 0.217 Watt*hr/kg) than that reported in U.S. Pat. No. 4,948,479(ie. 3,000 Watt*hr/kg).

The process of the present invention is useful for removing olefinic compounds from HCFC-141b using significantly less input power than any previously described photochlorination processes. These compounds are reacted out to form high boiling impurities which can then be easily separated from the HCFC-141b.

We claim:

1. In a process comprising (i) treating a liquid mixture of 1,1-dichloro-1-fluoroethane and at least one unsaturated carbon-containing compound with chlorine (ii) irradiating said chlorine-treated liquid mixture with ultraviolet light, thereby to selectively convert at least a portion of said at least one unsaturated carbon-containing compound to photochlorinated products thereof and (iii) separating said 1,1-dichloro-1-fluoroethane from said photochlorinated products, the improvement comprising conducting said irradiation of step (ii) with an ultraviolet light source having an ultraviolet radiation efficiency of 0.01 to 0.7 Einsteins\inch of arc\100 watts with an input power of 1.5 watts per inch of arc and whose radiation output is in the wavelength region that is substantially the same as the wavelength absorption band of chlorine.

2. In the process according to claim 1 wherein said ultraviolet efficiency is at least 0.01 Einsteins\inch of arc\100 watts input at a wavelength of from about 300 to about 400 mµ.

3. In the process according to claim 2 wherein said ultraviolet efficiency is at least 0.70 Einsteins\100 watts.

4. In the process according to claim 3 wherein the improvement further comprises carrying out said irradiation at a temperature of said irradiated chlorine-treated liquid mixture of from about 30 to about 100 Centigrade.

5. In the process according to claim 4 wherein the improvement further comprises carrying out said irradiation at a temperature of said irradiated chlorine-treated liquid mixture of from about 50 to about 65 Centigrade.

6. In the process according to claim 1, wherein the improvement further comprises using 20 to 120 watt mercury argon low pressure phosphor-coated fluorescent lamps having a maximum radiation output of from about 290 to about 335 nm and substantially no infra red output.

* * * * *